(12) United States Patent
Carnes et al.

(10) Patent No.: US 9,943,341 B2
(45) Date of Patent: Apr. 17, 2018

(54) RETENTION PLATE MEMBER FOR A SPINAL PLATE SYSTEM

(71) Applicant: K2M, Inc., Leesburg, VA (US)

(72) Inventors: Megan Carnes, Leesburg, VA (US); Todd Wallenstein, Ashburn, VA (US); Scott Jones, McMurray, PA (US)

(73) Assignee: K2M, LLC, Leesburg, VA (US)

( * ) Notice: Subject to any disclaimer, the term of this patent is extended or adjusted under 35 U.S.C. 154(b) by 600 days.

(21) Appl. No.: 13/943,724

(22) Filed: Jul. 16, 2013

(65) Prior Publication Data
US 2015/0025581 A1    Jan. 22, 2015

(51) Int. Cl.
*A61B 17/80* (2006.01)
*A61B 17/70* (2006.01)

(52) U.S. Cl.
CPC ........ *A61B 17/7059* (2013.01); *A61B 17/808* (2013.01); *A61B 17/8042* (2013.01)

(58) Field of Classification Search
CPC .................... A61B 17/8028; A61B 17/8033
See application file for complete search history.

(56) References Cited

U.S. PATENT DOCUMENTS

| | | | |
|---|---|---|---|
| 5,053,038 A * | 10/1991 | Sheehan | A61B 17/0642 606/75 |
| 5,643,265 A | 7/1997 | Errico et al. | |
| 5,735,853 A | 4/1998 | Olerud | |
| 6,030,389 A | 2/2000 | Wagner et al. | |
| 6,152,927 A | 11/2000 | Farris et al. | |
| 6,224,602 B1 | 5/2001 | Hayes | |
| 6,241,731 B1 | 6/2001 | Fiz et al. | |
| 6,258,089 B1 | 7/2001 | Campbell et al. | |
| 6,261,291 B1 | 7/2001 | Talaber et al. | |
| 6,331,179 B1 | 12/2001 | Freid et al. | |
| 6,383,186 B1 | 5/2002 | Michelson | |
| 6,402,755 B1 | 6/2002 | Pisharodi | |
| 6,425,903 B1 * | 7/2002 | Voegele | A61B 90/39 411/472 |
| 6,428,542 B1 | 8/2002 | Michelson | |
| 6,454,769 B2 | 9/2002 | Wagner et al. | |
| 6,533,786 B1 | 3/2003 | Needham et al. | |
| 6,575,975 B2 | 6/2003 | Brace et al. | |
| 6,592,586 B1 | 7/2003 | Michelson | |
| 6,599,290 B2 | 7/2003 | Bailey et al. | |
| 6,602,255 B1 | 8/2003 | Campbell et al. | |
| 6,626,907 B2 | 9/2003 | Campbell et al. | |
| 6,669,700 B1 | 12/2003 | Farris et al. | |
| 6,679,883 B2 | 1/2004 | Hawkes et al. | |
| 6,695,846 B2 | 2/2004 | Richelsoph et al. | |
| 6,945,973 B2 | 9/2005 | Bray | |
| 6,945,974 B2 | 9/2005 | Dalton | |
| 6,945,975 B2 | 9/2005 | Dalton | |

(Continued)

*Primary Examiner* — Jan Christopher Merene
*Assistant Examiner* — Atiya Mahmud
(74) *Attorney, Agent, or Firm* — Carter, DeLuca, Farrell & Schmidt, LLP

(57) ABSTRACT

A retention member for a spinal plate system where at least one or more segments of the retention member cover the head portion of a bone anchor member to inhibit movement of the bone anchor member that is inserted into the plate. The retention member allows for ease of insertion of the bone anchor member and once the bone anchor member is fully seated the retention member is in place.

11 Claims, 18 Drawing Sheets

(56) References Cited

U.S. PATENT DOCUMENTS

| | | |
|---|---|---|
| 6,964,664 B2 | 11/2005 | Freid et al. |
| 6,979,334 B2 | 12/2005 | Dalton |
| 7,001,387 B2 | 2/2006 | Farris et al. |
| 7,001,389 B1 | 2/2006 | Navarro et al. |
| 7,004,944 B2 | 2/2006 | Gause |
| 7,025,769 B1 | 4/2006 | Ferree |
| 7,048,739 B2 | 5/2006 | Konieczynski et al. |
| 7,175,624 B2 | 2/2007 | Konieczynski et al. |
| 7,452,370 B2 | 11/2008 | Anderson |
| 7,481,811 B2 | 1/2009 | Suh |
| 7,524,325 B2 | 4/2009 | Khalili |
| 7,611,527 B2 | 11/2009 | Freid et al. |
| 7,651,517 B2 | 1/2010 | Konieczynski et al. |
| 7,666,185 B2 | 2/2010 | Ryan et al. |
| 7,699,880 B2 | 4/2010 | Orbay et al. |
| 7,740,649 B2 | 6/2010 | Mosca et al. |
| 7,887,547 B2 | 2/2011 | Campbell et al. |
| 7,909,859 B2 | 3/2011 | Mosca et al. |
| 7,909,860 B2 | 3/2011 | Rathbun et al. |
| 7,914,561 B2 | 3/2011 | Konieczynski et al. |
| 7,981,142 B2 | 7/2011 | Konieczynski et al. |
| 7,993,380 B2 | 8/2011 | Hawkes |
| 8,696,715 B2 * | 4/2014 | Sidebotham ....... A61B 17/8047 606/290 |
| 2003/0105462 A1 | 6/2003 | Haider |
| 2003/0225409 A1 | 12/2003 | Freid et al. |
| 2004/0019353 A1 | 1/2004 | Freid et al. |
| 2004/0127896 A1 | 7/2004 | Lombardo et al. |
| 2004/0181227 A1 | 9/2004 | Khalili |
| 2004/0204712 A1 | 10/2004 | Kolb et al. |
| 2005/0021032 A1 * | 1/2005 | Koo ................... A61B 17/7059 606/295 |
| 2005/0049595 A1 | 3/2005 | Suh et al. |
| 2005/0107796 A1 | 5/2005 | Gerlach et al. |
| 2005/0192577 A1 * | 9/2005 | Mosca ............... A61B 17/1615 606/86 B |
| 2005/0251137 A1 | 11/2005 | Ball |
| 2006/0122604 A1 | 6/2006 | Gorhan et al. |
| 2006/0155285 A1 | 7/2006 | Anderson |
| 2006/0200147 A1 | 9/2006 | Ensign et al. |
| 2006/0235403 A1 | 10/2006 | Blain |
| 2006/0235409 A1 | 10/2006 | Blain |
| 2006/0235411 A1 | 10/2006 | Blain et al. |
| 2007/0123879 A1 | 5/2007 | Songer et al. |
| 2007/0233120 A1 | 10/2007 | Thramann et al. |
| 2008/0097442 A1 | 4/2008 | Dixon |
| 2008/0147124 A1 | 6/2008 | Haidukewych et al. |
| 2008/0161862 A1 | 7/2008 | Ensign |
| 2008/0215097 A1 | 9/2008 | Ensign et al. |
| 2008/0243192 A1 | 10/2008 | Jacene et al. |
| 2008/0288000 A1 | 11/2008 | Cawley |
| 2008/0288001 A1 | 11/2008 | Cawley et al. |
| 2009/0012571 A1 | 1/2009 | Perrow et al. |
| 2009/0054930 A1 | 2/2009 | Aflatoon |
| 2009/0062863 A1 | 3/2009 | Peppers |
| 2009/0129889 A1 * | 5/2009 | Woodall ................ F16B 37/041 411/433 |
| 2009/0149856 A1 | 6/2009 | Paakinaho et al. |
| 2009/0149888 A1 | 6/2009 | Abdelgany |
| 2009/0182383 A1 | 7/2009 | Prybyla et al. |
| 2010/0121383 A1 | 5/2010 | Stanaford et al. |
| 2010/0222780 A1 | 9/2010 | Lindemann et al. |
| 2010/0241174 A1 * | 9/2010 | Robinson ............ A61B 17/8042 606/289 |
| 2011/0029023 A1 | 2/2011 | Tornier |
| 2012/0065690 A1 * | 3/2012 | Perrow ............. A61B 17/7059 606/294 |

\* cited by examiner

SECTION B-B
SCALE 8:1

RETENTION PLATE MEMBER FOR A SPINAL PLATE SYSTEM

TECHNICAL FIELD

The present disclosure relates generally to surgical procedures and methods for use in orthopedic spinal procedures, most specifically for use in the fixation of the cervical spine. The disclosure pertains to a bone anchor and plating system with bone anchor retention means for use in a system for fixing at least two adjacent bone segments in the human spine.

BACKGROUND

Disease, the effects of aging, or physical trauma resulting in damage to the spine has been treated in many instances by fixation or stabilization of the effected vertebra. The use of plates and screws for fixation and stabilization of the vertebra has been widely accepted as a reliable practice and has proven to be highly successful clinically for both fracture (trauma) and spinal fusion applications. The vertebral plates, which are attached to the anterior portion of the vertebral bodies of the spinal column by bone screws have some common features such as relatively planar body profiles that define multiple holes or slots through which the screws fit and are threaded into the bone. Innovations over time have been primarily directed to improving the dependable security of the bone screws to the plate and as such have resulted in virtually complete rigidity of the screw, bone plate, bone connection. Various means have been used to prevent the screws from becoming loose or detached from their necessary secured or locked attachment to the vertebral plate. Among the differences between the conventionally used plates and screws is the manner in which the screws are locked into place in the hole or slot of the plate after the screws have been secured to the bone.

Early plate designs consisted of bone plates having holes through which screws were passed and secured into the bone. These plates had no special provision for attaching the screws to the plate and as such were susceptible to having the screws back out of the plate over time. There have been clinically reported instances of screws backing out of these type plates with resulting surgical complications. Due to the potential and actual unreliable performance of such plates, the need for secure fixation of the screw to the plate as well as to the bone is now considered a basic requirement for vertebral plates.

One approach to prevent such screw backing out has been to provide features in and on the plate which are specifically designed to hold the screw in position once the screw is inserted through the plate and screwed into the bone. One design option is a cover plate as indicated in U.S. Pat. No. 7,137,984 by Michelson which typically adds thickness to the plate by design. A thicker plate creates more post-operative issues for the patient especially in the cervical spine where the esophagus can easily become aggravated and damaged by the thicker plate designs. Another direction taken in this effort has been to design plates that incorporate or attach individual retaining rings or snap features associated with each plate hole configuration to hold the inserted screw in place relative to the plate, such as that depicted in US2010/0241174 by Robinson. While designs such as US2010/0241174 by Robinson provide improved screw security over a plate with no retention feature with reduced thickness compared to cover designs such as Michelson, applicants have determined that there is room for improvement with respect to screw security in the Robinson design. Therefore a need exists for an optimal way to reliably retain the screw, while not increasing plate thickness.

SUMMARY

In accordance with the purposes of this disclosure, a vertebral plating system, or more specifically a bone screw, retention ring and plate system is disclosed that includes an implant having a plate which defines a plurality of transversely extending orifices that are configured to receive a bone anchor for engaging the plate to the spine. One or more retention members, having an elliptical, oval, rectangular, square, or other shape, can be positioned within a recess of the orifice wall such that portions of the retention member(s) extend into a portion of each orifice to retain a bone anchor therein.

The bone anchor member preferably contains a head portion and a threaded shank portion. The retention member should not create undue torque when inserting the bone anchor member into the orifice and past the retention member such that the head of the bone anchor member is under the retention member. The bone anchor member may be inserted concentrically into the orifice or at an angle. Depending upon the angle of insertion of the bone anchor member, various portion(s) of the retention member will provide contact to the bone anchor member head portion and prevent movement of the bone anchor.

BRIEF DESCRIPTION OF THE DRAWINGS

Various embodiments of the present disclosure are described herein with reference to the drawings wherein.

DETAILED DESCRIPTION

In the following description, as is traditional, the term "proximal" refers to a portion of a surgical instrument closer to the operator while the term "distal" refers to a portion of a surgical instrument farther from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1:
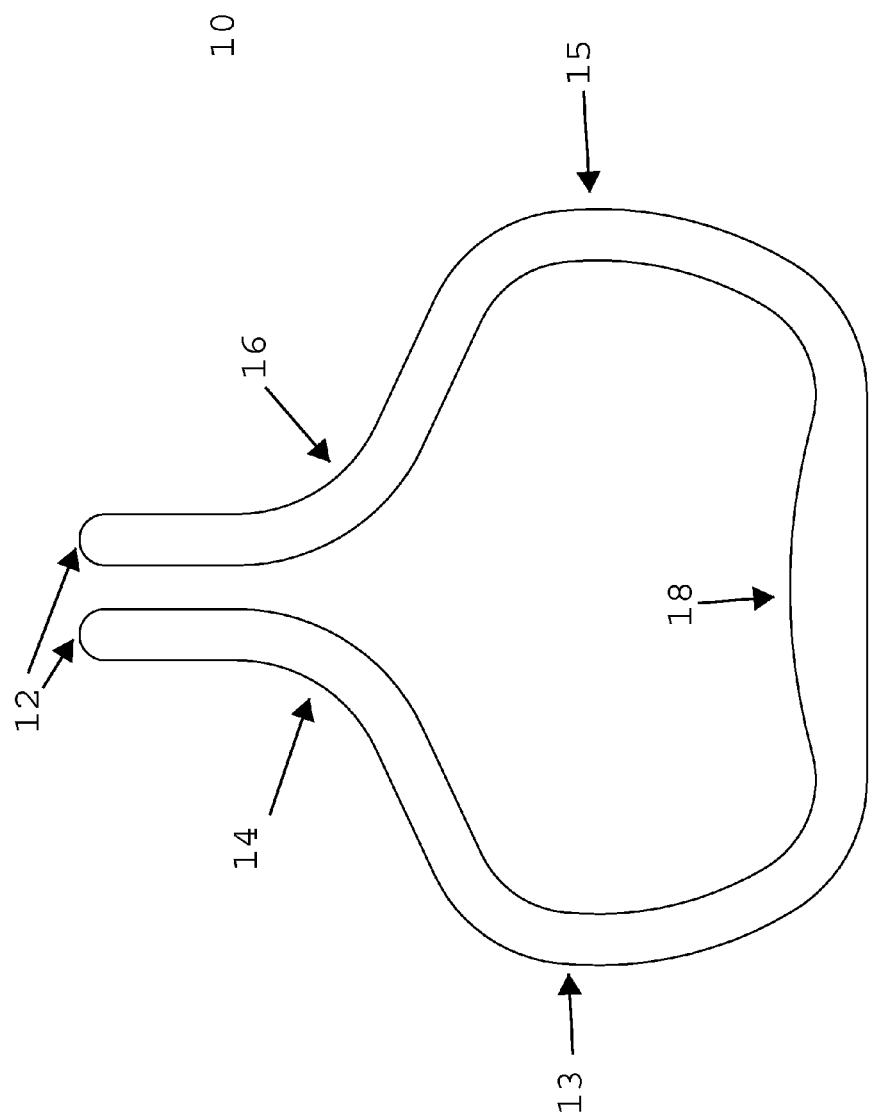
FIG. 1 is a top view of the preferred retention member.
Figure 2:
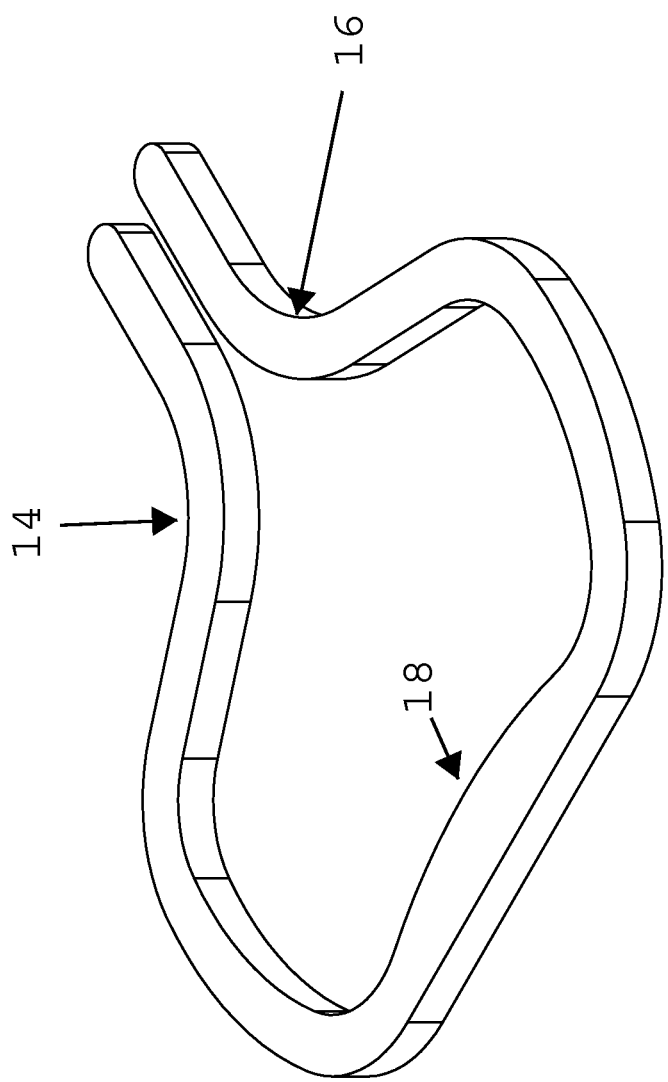
FIG. 2 is an isometric view of the preferred retention member.
Figure 3:
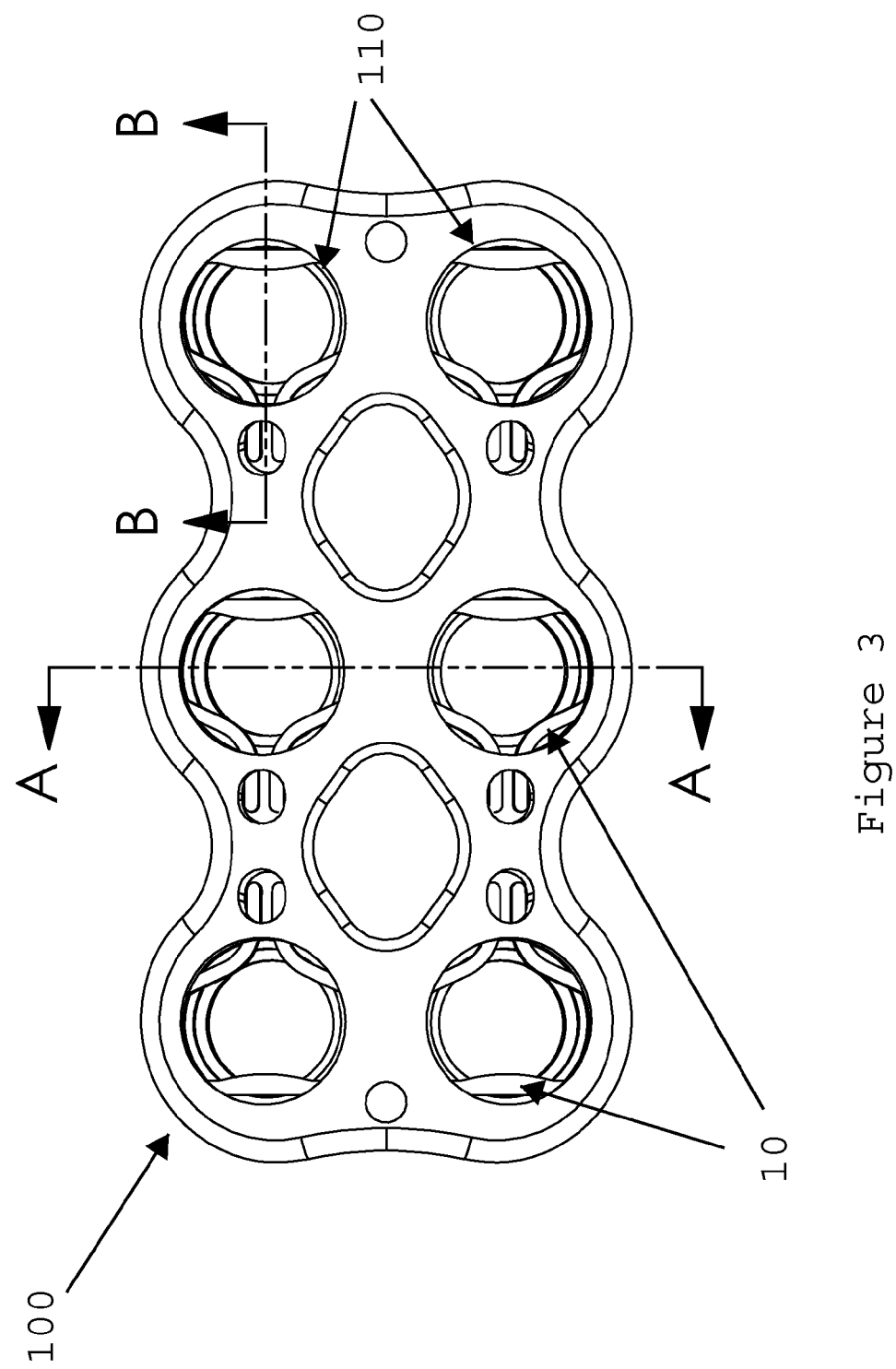
FIG. 3 is a top view of the plate with retention members.
Figure 4:
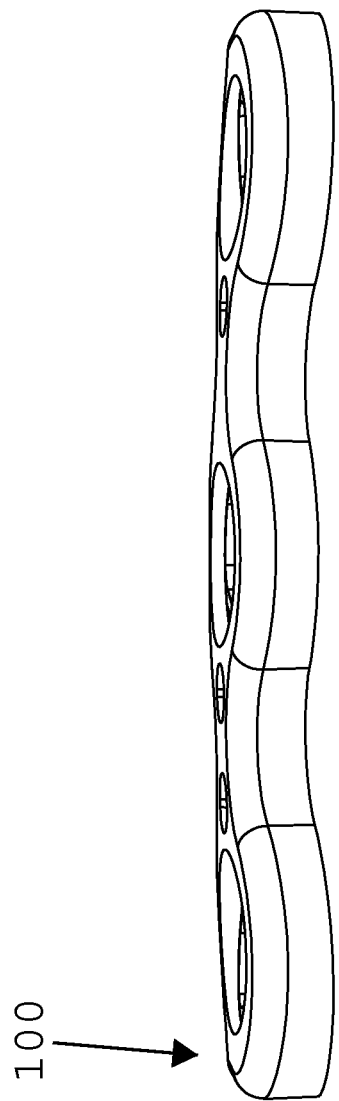
FIG. 4 is a side view of the plate.
Figure 10:
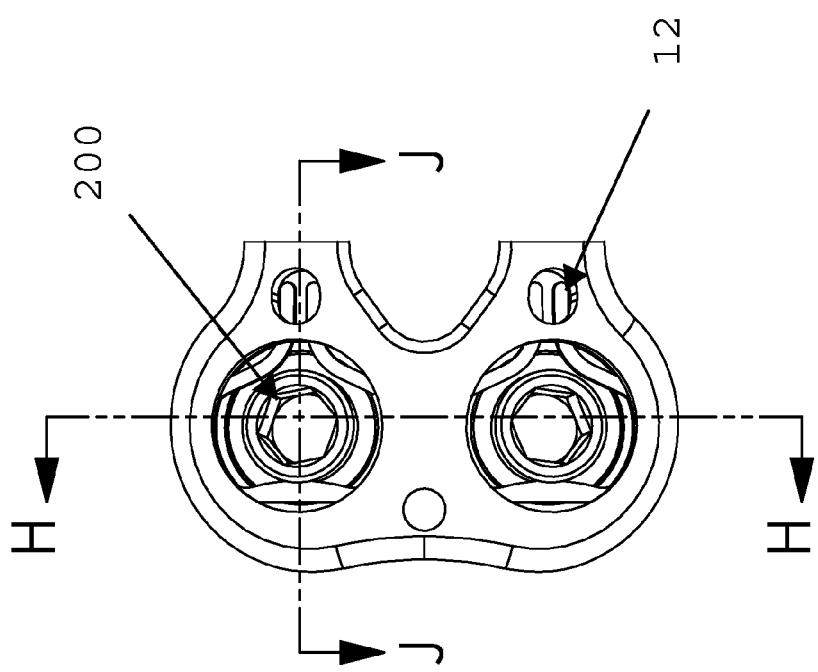
FIG. 10 is a partial top view of the plate with retention members.

With reference to FIGS. 1-2, the preferred retention member 10 consists of three inwardly curved tab sections 14, 16 and 18 which are connected by outwardly curved connecting sections 13, 15. Arm sections 12 are provided at each end of the retention member in opposed facing relationship with a gap defined therebetween. When retention member 10 is disposed in a recess within the plate, the inwardly curved tab sections 14, 16 and 18 protrude into the orifice 110 of the plate 100 as indicated in FIG. 3. When a bone anchor member 200 is fully inserted into at least one of the orifice(s) 110 at least one of the inwardly curved tab sections 14, 16 and 18 will reside on the top of the head portion 210 of the bone anchor member 200 (see FIGS. 10-11) to prevent proximal movement of the bone anchor member 200. That is, retention member 10 prevents the anchor member from backing out of the plate. The retention member 10 may be formed monolithically or from multiple components and may be made from various biocompatible materials, including but not limited to stainless steel, titanium, nickel-titanium (nitinol) cobalt chrome and various polymers (PEEK, polyurethane, polycarbonate etc). The retention member 10 may be formed by die cutting material, machining (EDM, milling etc), forming or other known methods.

Figure 5:
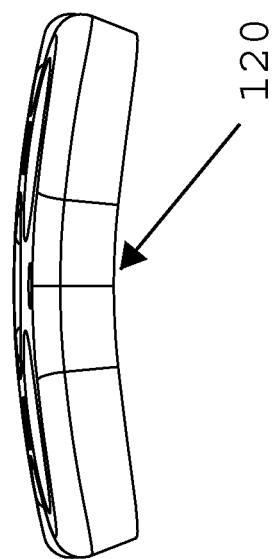
FIG. 5 is an end view of the plate.
Figure 6:
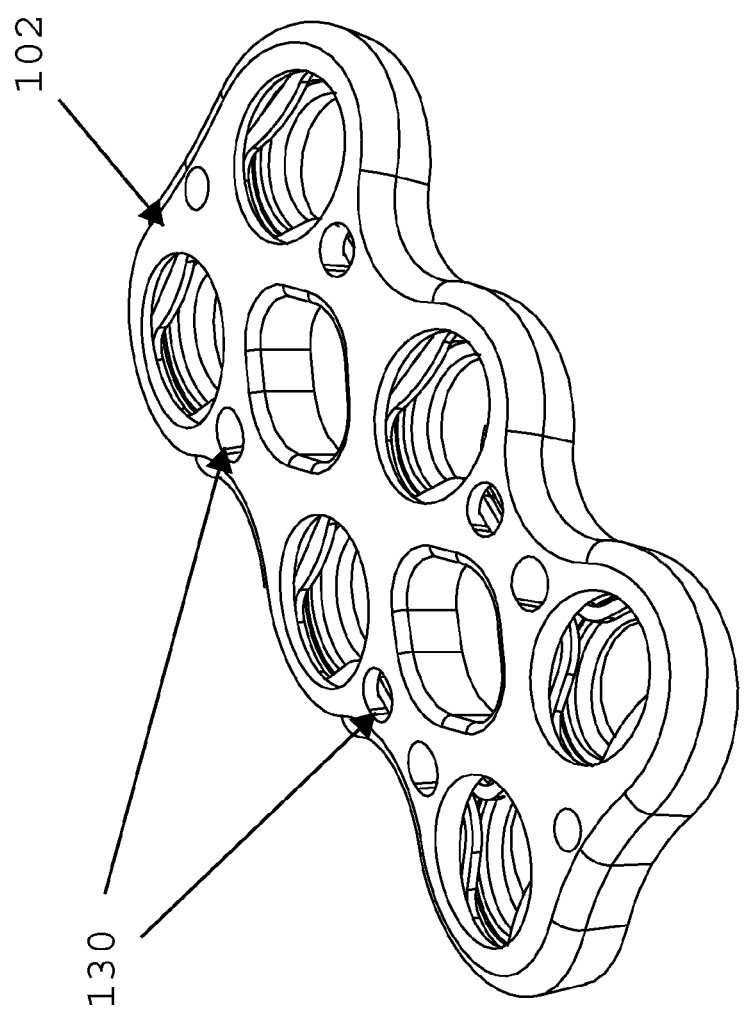
FIG. 6 is an isometric view of the plate with retention members.
Figure 7:
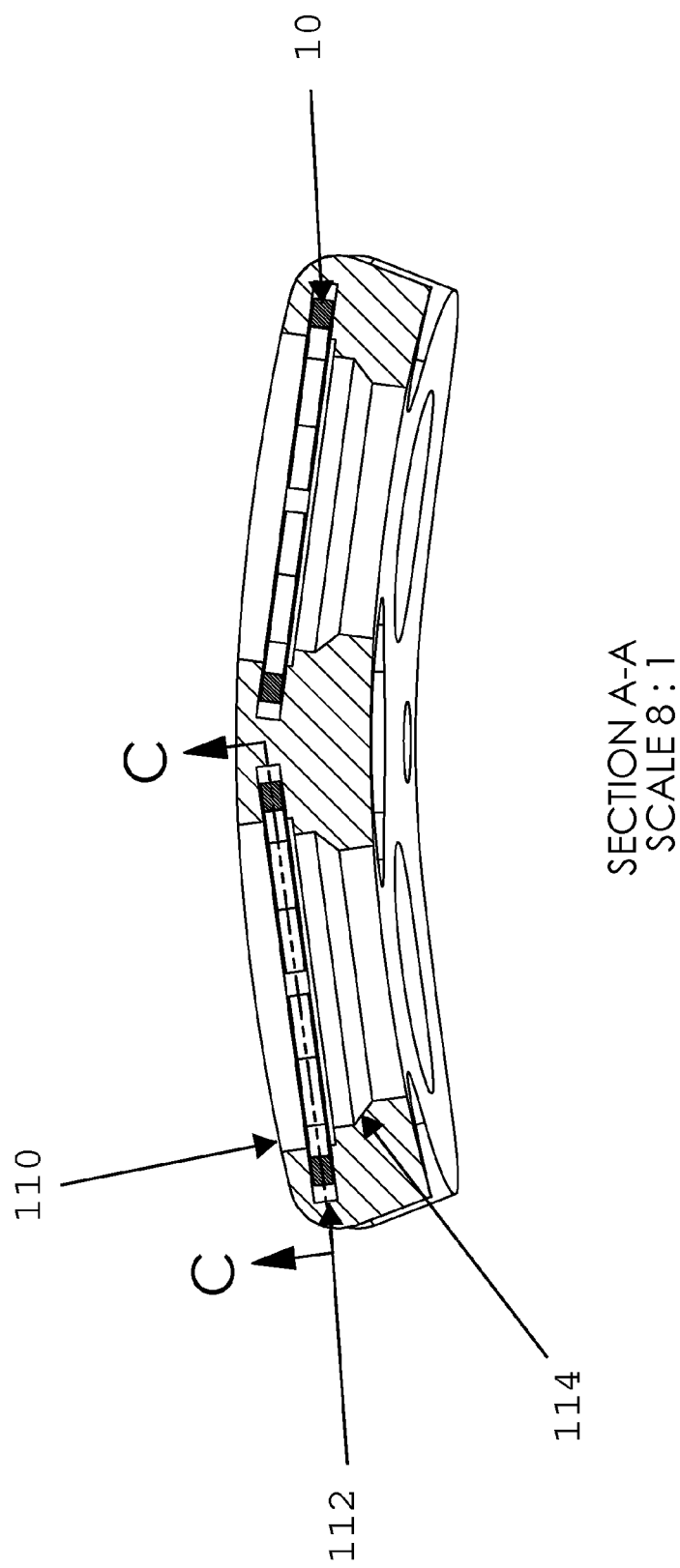
FIG. 7 is a section view taken along section A-A from FIG. 3.
Figure 8:
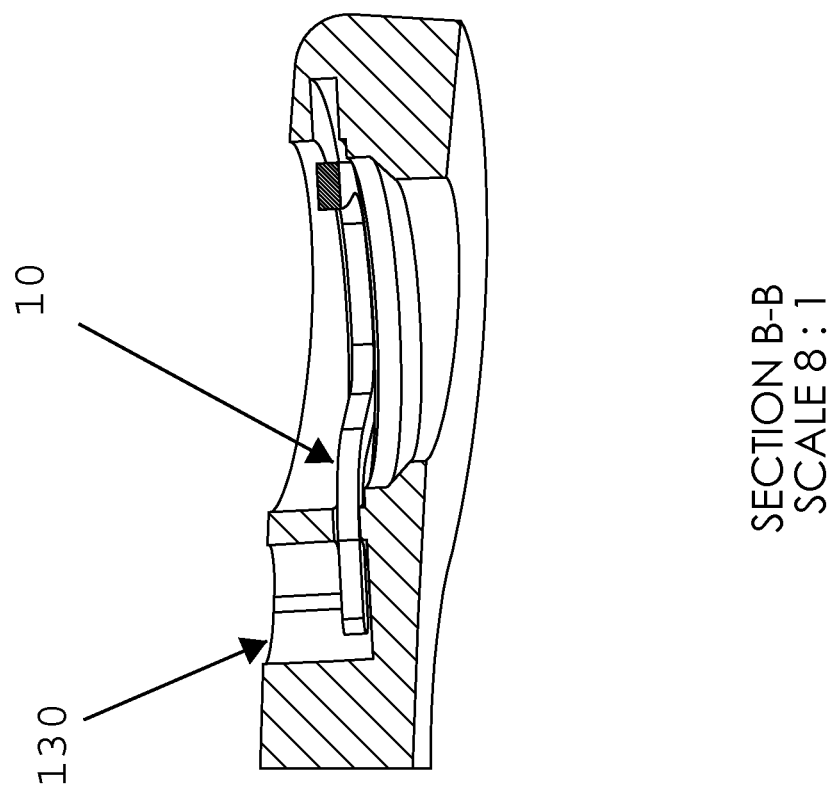
FIG. 8 is a section view taken along section B-B from FIG. 3.

The plate member 100 may be one of a variety of orthopedic plates, including but not limited to a spinal plate, including a lumbar plate, a thoracic plate and a cervical plate which may span one or more vertebrae. The plate illustrated herein is configured and dimensioned to span two intervertebral spaces and be secured to three vertebral bodies, but it is contemplated that the retention member of the present disclosure may be used on plates secured to as few as one vertebral body or four or more vertebral bodies. The plate member 100 contains one or more orifices 110 which are substantially perpendicular to the top surface of the plate 102. The plate member 100 may be curved to match the anatomy as indicated in FIG. 5 by curvature 120. At least one or more of the orifices 110 contain a recess 112 feature on the inner wall of the orifice 110 as indicated in FIG. 7. This recess 112 is used to contain the retention member 10. In addition, plate member 100 also contains a visualization orifice(s) 130 to indicate the presence of retention member 10 in the plate.

The retention member 10 provides optimal retention properties for keeping the bone anchor 200 in place regardless of the angle of insertion of the bone anchor 200 into the orifice 110. In addition, the retention member 10 does not increase the insertion force required to insert the bone anchor 200 which is an important user requirement and also eliminates the potential for damaging the retention member 10 during insertion of the bone anchor 200. Bone anchors are inserted into bone through the plate orifices in a known manner such as by drilling, tapping and driving the bone anchor into bone, such as by screwing threads into bone. Alternatively, the bone anchor may include threads that are self-tapping.

FIGS. 14-18 exhibit the screw insertion and removal tool 400 which has a knurled and/or textured proximal end 410 to facilitate grasping and rotating of the instrument. The distal end of the instrument contains two arm members 402 which are inserted into the screw orifice 110, and when the screw insertion and removal tool 400 is rotated approximately 90 degrees the arm members 402 push the retention member 10 further into the recess 112 so that access can be achieved to the hex feature 216 on the screw head 210. While the screw insertion and removal tool 400 is rotated and keeping the retention member 10 in the recess 112, a 2.5 tapered hex driver (not shown, or other like instrument) can be inserted through the cannula 404 of the screw insertion and removal tool 400 and engage the head of the screw 210 and then rotated for either insertion of the screw 200 or removal of the screw 200. Once the screw 200 is fully seated into the plate 100, the hex driver can be removed and the screw insertion and removal tool 400 rotated in the opposite direction to allow the retention member 10 to spring back into its prior location within the orifice 110 and reside on the top of the screw head 210. If the screw 200 was removed, then the retention member 10 would spring back into the orifice 110 where it was prior to use of the screw insertion and removal tool 400.

Figure 13:
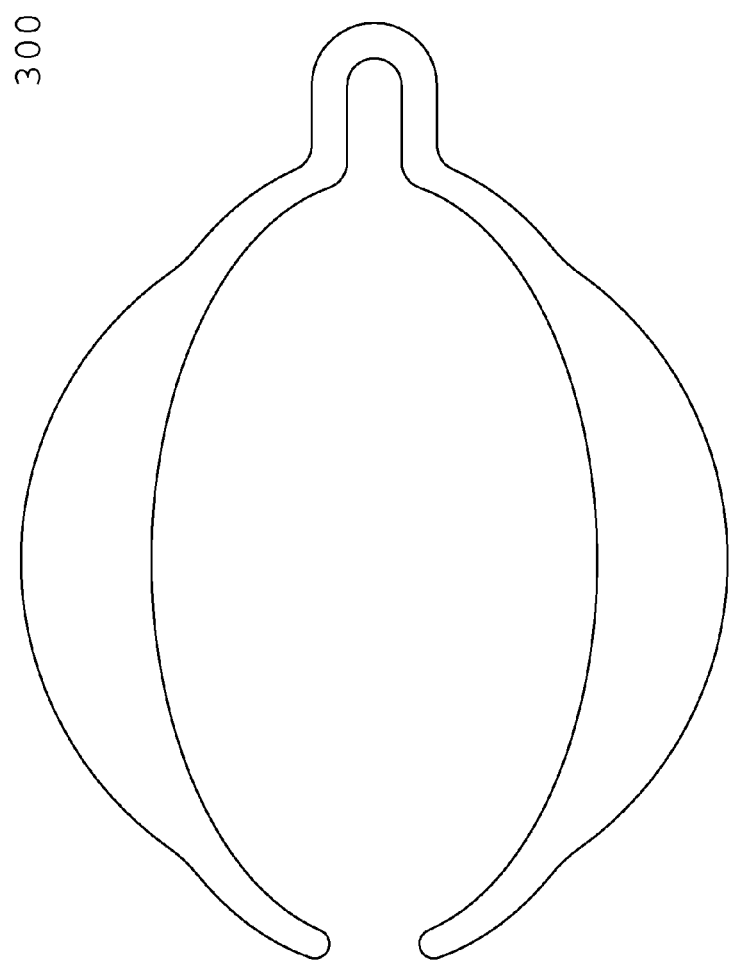
FIG. 13 depicts a C shaped retention ring in accordance with Robinson US2010/0241174.
Figure 14:
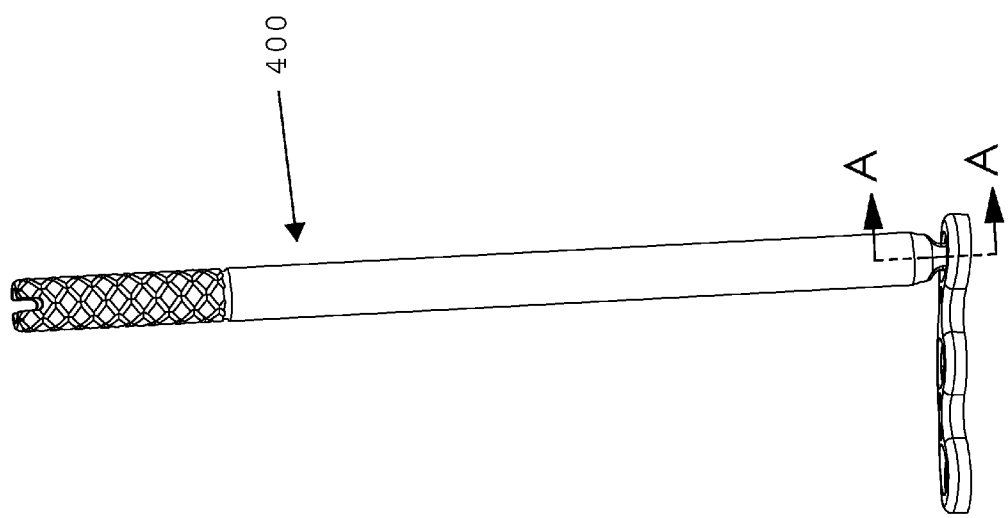
FIG. 14 depicts a screw insertion and removal tool inserted into the plate.
Figure 15:
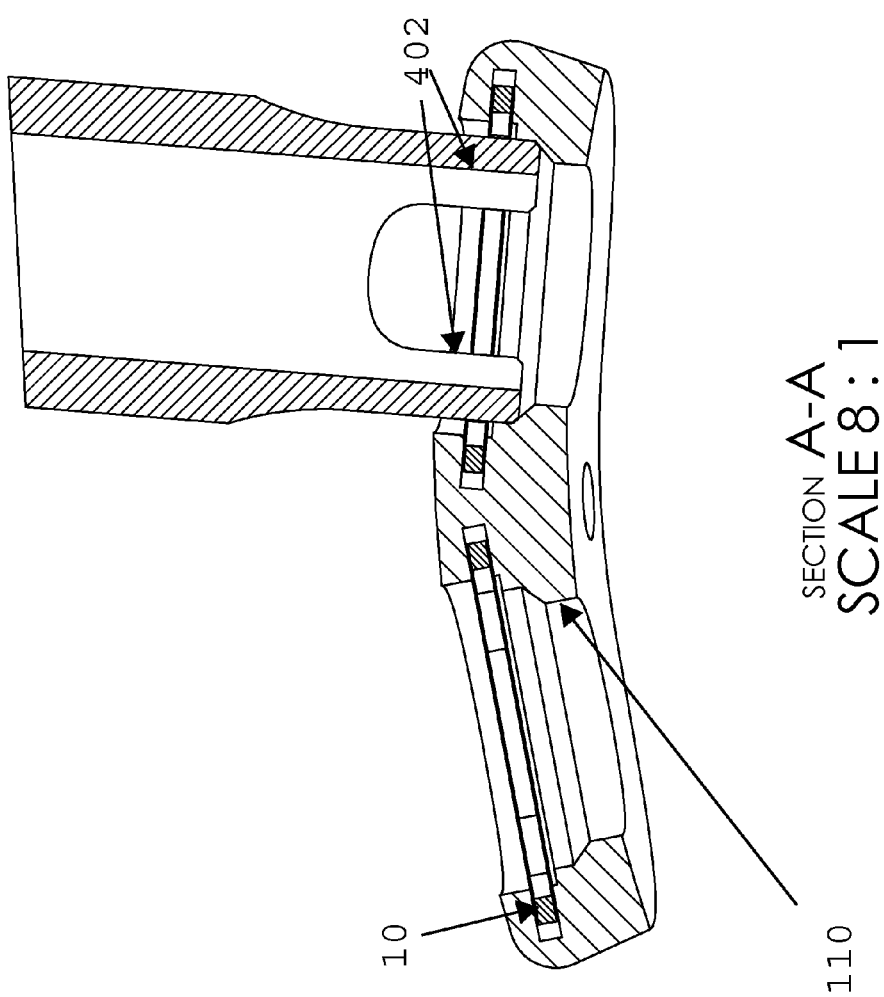
FIG. 15 depicts a close up view taken along section A-A.
Figure 16:
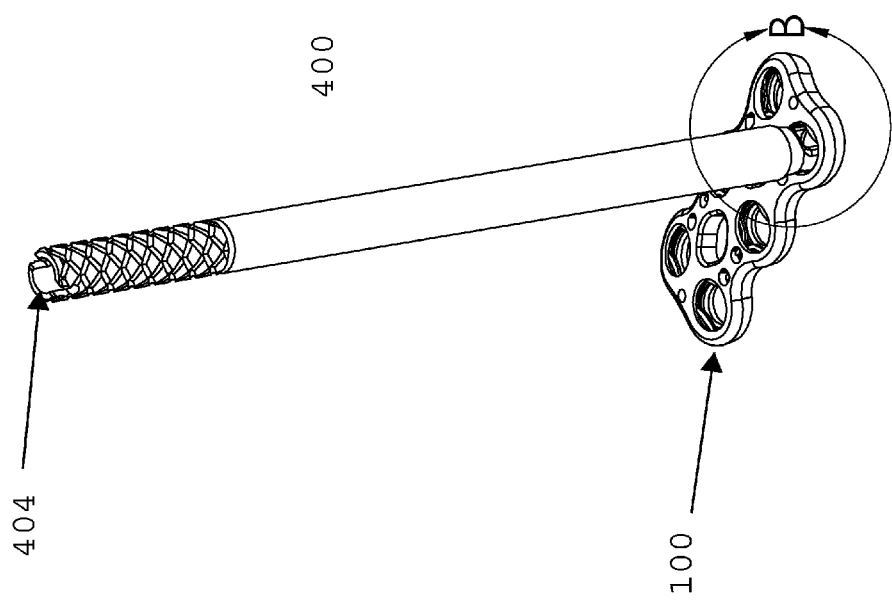
FIG. 16 depicts a screw removal tool inserted into the plate.
Figure 17:
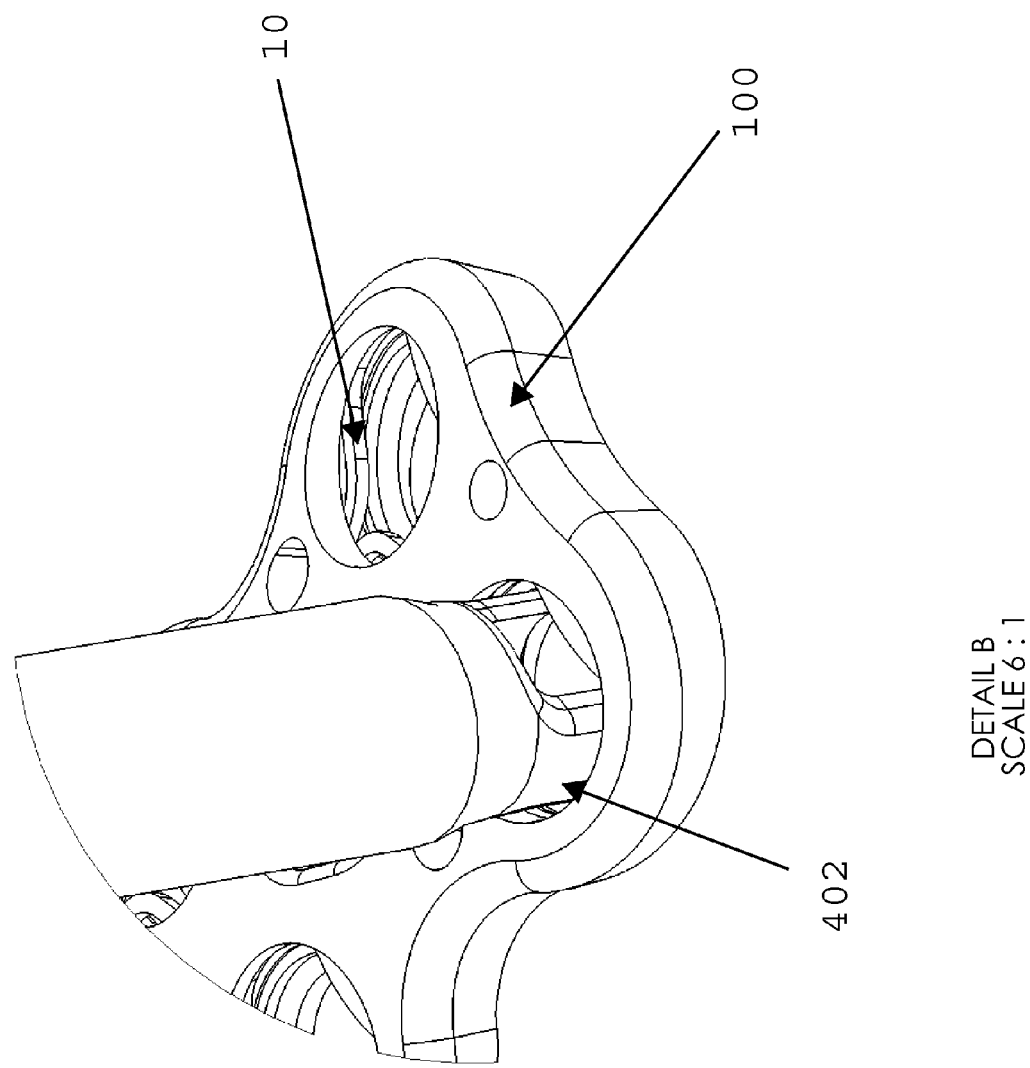
FIG. 17 depicts a close up view taken of detail B.
Figure 18:
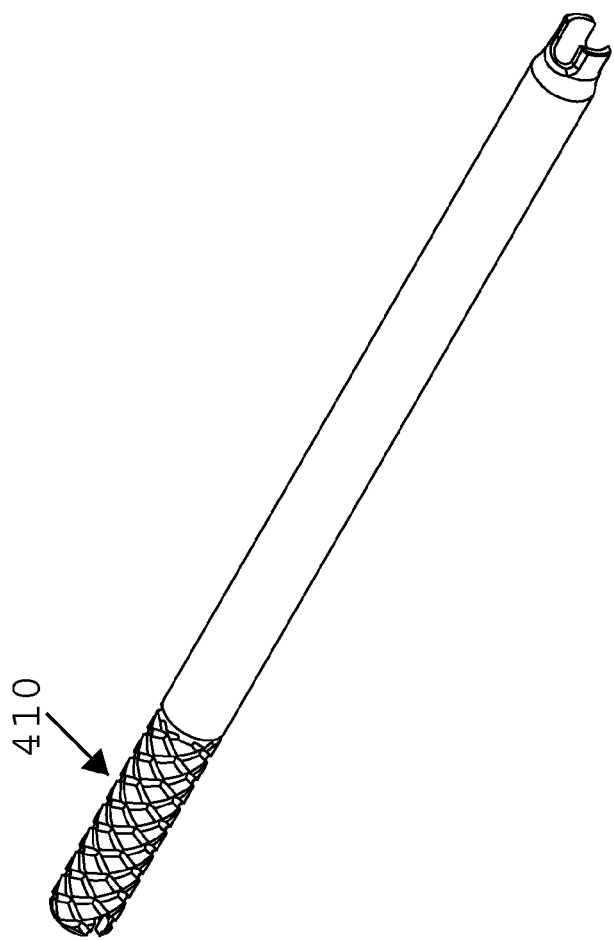
FIG. 18 depicts an isometric view of the screw insertion and removal tool.

Comparative testing was conducted to compare the torque limit values of the retention member 10 of the present disclosure to a C-shaped retention member 300 of the type shown and described in Robinson US 2010/0241174, and illustrated as C shaped retention ring 300 in FIG. 13. The test results are set forth in Table 1 which indicates the torque limit values in inch pounds, below, with the designation K2-39-1009-01 representing test results conducted with the C-shaped ring of FIG. 13 and the designation XP-820-01 representing tests conducted with the retention member of the present disclosure. As shown, the C-shaped ring had a torque limit removal force value of 1.86 inch-pounds when the screws are inserted at an Angle (15 degrees to normal) to the hole of the plate, whereas the preferred retention ring 10 demonstrated torque limit retention values of 5.93 inch-pounds when all three tab sections (14, 16 and 18) were engaged with the bone anchor head and 5.29 inch-pounds when only tab sections 14 and 16 were engaged and 9.75 inch-pounds when only tab section 18 was engaged with the screw head. The insertion force of XP-820-01 had the following torque limit values: 7.04 inch-pounds and 6.12 inch-pounds for the angled 1 and angled 2 tests and 6.54 inch-pounds for the concentric screw test respectively. These insertion force results are comparable to the insertion force for C-shaped rings and other screw-plate retention mechanisms, and demonstrate that the insertion force for the retention member disclosed herein are acceptable.

In summary, the data in Table 1 shows that the concentrically placed screws for both K2-39-1009-01 and the XP-820-01 devices exhibited removal values that were not statistically different In addition, the data indicates that when screws are inserted at an angle the retention member of the present disclosure demonstrates substantially improved removal force compared to the C-shaped design. Overall, the XP-820-01 design performed superiorly to the K2-39-1009-01 design with respect to failure mode and removal force. It also was observed that with the retention member of the present disclosure the higher removal force resulted in damage to the screw or the retention member before the screw could be backed out, indicating optimal prevention of screw back out. Other mechanisms permit the screw to back out or the ring to fail at lower forces, providing less secure back out prevention. Based on tests conducted with the preferred retention member, applicants conclude that the preferred three tab design can resist screw back out when just two tabs overlay the screw head and up to 4 to 7 inch pounds of removal force is applied. Similarly, applicants conclude that the preferred three tab design can resist screw back out when all three tabs overly the screw head and up to 8 to 11 inch pounds of removal force is applied.

TABLE 1

Test data for insertion force and retention force of retention ring designs.

| Part | Screw Angulation | Average Insertion (inch-pounds) | Average Removal (inch-pounds) |
| --- | --- | --- | --- |
| K2-39-1009-01 | Angled | N/A | 1.86 |
| K2-39-1009-01 | concentric | 2.66 | 5.05 |
| XP-820-01 | Angled 1 | 7.04 | 9.75 |
| XP-820-01 | Angled 2 | 6.12 | 5.29 |
| XP-820-01 | Angled 1/2 | N/A | 5.93 |
| XP-820-01 | concentric | 6.54 | 4.67 |

Figure 9:
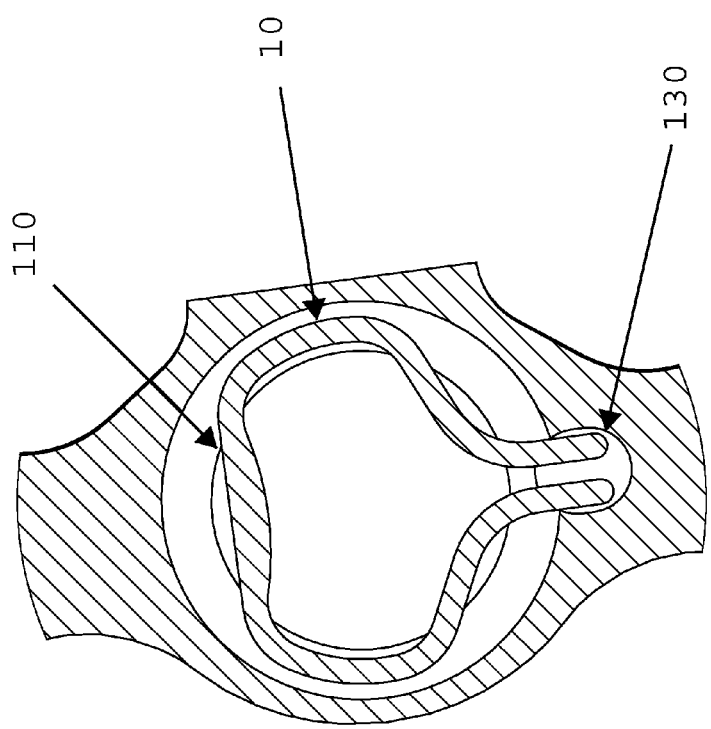
FIG. 9 is a section view taken along section C-C from FIG. 7.
Figure 11:
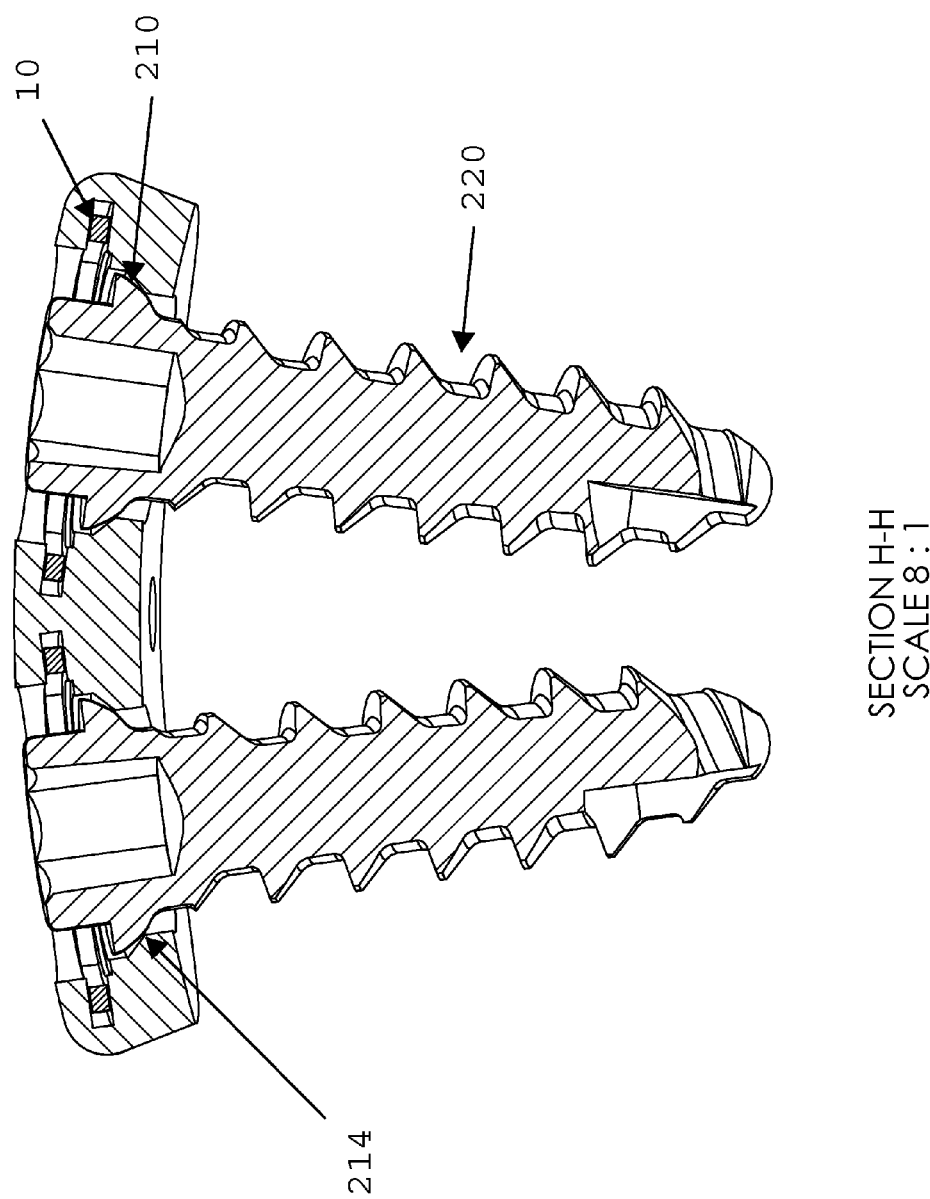
FIG. 11 is section view taken along section H-H from FIG. 10.
Figure 12:
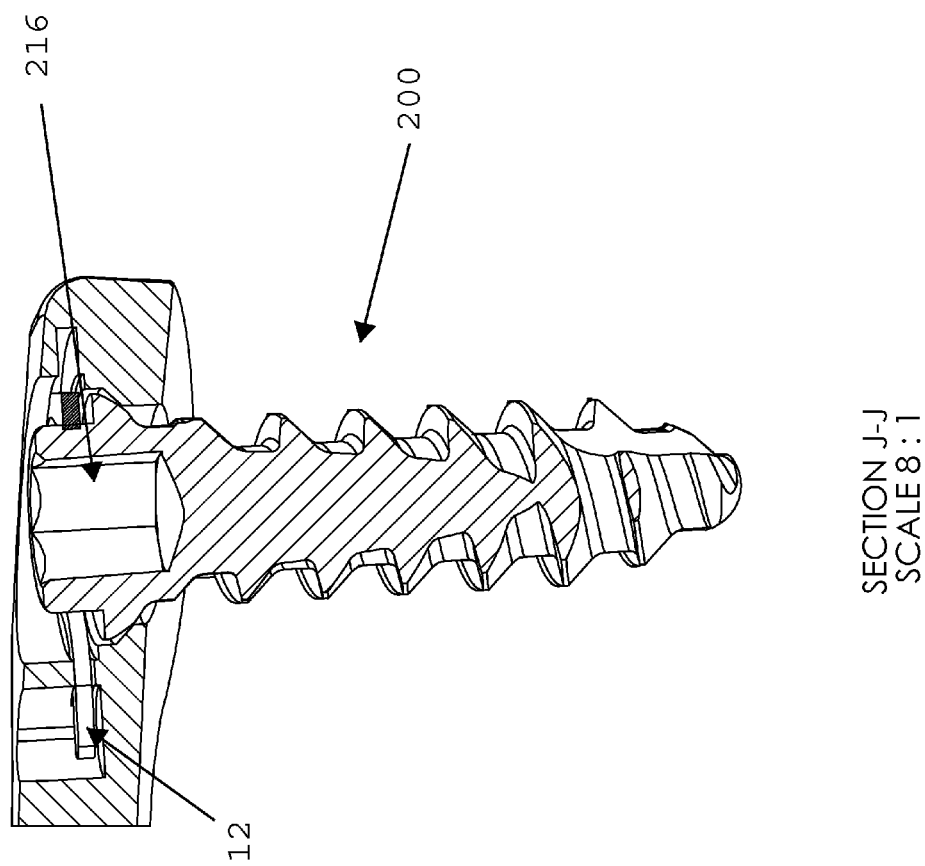
FIG. 12 is section view taken along section J-J from FIG. 10.

The design of retention ring 10 is best indicated in FIGS. 1-12. FIG. 3 exhibits a top view of the plate assembly with visualization of the two arm members 12 of each retention ring 10 through the visualization orifices 130. FIG. 7 indicates a section view along line A-A from FIG. 3 which bisects the plate in a cranial-caudal direction and through the center of two orifices 100 for the bone anchors 200. As can be noted in FIG. 7, item 112 is the annular recess feature in the plate that accommodates the retention ring 10. The retention ring 10 is compressed into the center of the orifice 100 and then placed down into the orifice adjacent to the recess 112 and released. The retention ring 10 is made of such a material that it "springs" back open and into the recess 112. It is this springiness that also allows the screw 200 to be inserted through its center and then spring back to cover the top of the screw head 210 once the screw 200 has been fully seated into the plate 100 and chamfer 114 on the plate mates with chamfer 214 of the underside of the screw head. FIG. 9 depicts a section view along section line C-C from FIG. 7. As noted in FIG. 9 the ring 10 resides in the recess 112, whereby the recess 112 is a larger diameter than the orifice 110 of the plate 100 so that the ring 10 is captured inside the plate 100. FIG. 11 depicts a cross section taken along section line H-H of FIG. 10. Here the screw 200 is fully seated into the orifice 110 of the plate 100 and below the retaining ring 10.

In use, the retention rings members are pre-assembled into the plate. The plate is then put in place against the vertebral bodies and the screws are inserted through the plate and into the vertebral bodies. The screws may be inserted at an angle to the hole not concentric to the hole. The screw heads push open the ring at its center and pass through the retention ring during their insertion into the orifice(s) of the plate as the screw is driven into bone under the plate. The ring resiliently returns back to its original shape and with the inwardly curved blocking tabs residing over portions of the screw head after the screw head passes the retention member. The retention ring will contact the surface of the screw head at one or more of the ring tab sections which provide force on the screw head to mitigate the screw from backing out of the plate. Preferably, where three inwardly curved blocking tab portions are used, the tabs will overly the screw head at approximately 15 degrees, 345 degrees and 180 degrees, respectively.

While several embodiments of the disclosure have been shown in the drawings and/or discussed herein, it is not intended that the disclosure be limited thereto, as it is intended that the disclosure be as broad in scope as the art will allow and that the specification be read likewise. By way of example only, the preferred retention member is shown having three inwardly curved blocking tab sections, but it is contemplated that a different number of inwardly curved blocking tab sections may be used. Therefore, the above description should not be construed as limiting, but merely as exemplifications of particular embodiments. Those skilled in the art will envision other modifications within the scope and spirit of the claims appended hereto.

The invention claimed is:

1. A plate assembly, comprising:
a plate member having orifices and visualization orifices defined therethrough, each visualization orifice disposed adjacent a respective orifice, the plate member defining channels interconnecting respective orifices and visualization orifices, wherein each orifice is configured to receive a corresponding bone anchor member therethrough; and
a retention member, comprising:
a plurality of inwardly curved blocking tab sections connected to each other by outwardly curved connecting sections, the retention member defining a longitudinal axis;
a linearly extending intermediary section connecting the outwardly curved connecting sections, the linearly extending intermediary section defining an inwardly curved blocking tab section and a planar surface opposite thereto; and
arm sections at each end of the retention member, each arm section extending linearly from a respective inwardly curved blocking tab section along the longitudinal axis and terminating at respective end portions disposed opposite the outwardly curved connection sections,
wherein the arm sections are parallel to and spaced apart from each other, the end portion of each arm section configured to be slidably received within a respective channel and visualization orifice of the plate member such that at least a portion of the end portion of each arm section is visible through the visualization orifice.

2. The plate assembly of claim 1, wherein the retention member is configured to be operatively disposed within an orifice.

3. The plate assembly of claim 2, wherein each orifice is configured and dimensioned to receive a bone anchor member comprising:
a head portion; and
a threaded shank portion,
wherein one or more of the inwardly curved blocking tab sections of the retention member is configured and dimensioned to cover a portion of the head portion of the bone anchor member.

4. The plate assembly of claim 3, wherein first and second inwardly curved blocking tab sections of the retention member are configured and dimensioned to cover respective first and second portions of a bone anchor member and prevent longitudinal movement thereof.

5. The plate assembly of claim 4, wherein the retention member further comprises a third inwardly curved blocking tab section, the first, second, and third inwardly curved blocking tab sections configured and dimensioned to cover respective first, second, and third portions of a head of a bone anchor member.

6. The plate assembly of claim 5, wherein the first, second, and third inwardly curved blocking tab sections of the retention member are configured to prevent longitudinal movement of a bone anchor member when a removal force between 8 inch-pounds and 11 inch-pounds is applied thereto.

7. The plate assembly of claim 4, wherein the first and second inwardly curved blocking tab sections of the retention member are configured and dimensioned to cover respective portions of a bone anchor member and resist screw removal when a removal force between 4 inch-pounds and 7 inch-pounds is applied thereto.

8. The plate assembly of claim 4, wherein the plurality of inwardly curved blocking tab sections further comprise first second, and third inwardly curved blocking tab sections configured and dimensioned to cover portions of a head portion of a bone anchor member at approximately 15 degrees, 345 degrees, and 180 degrees, respectively.

9. The plate assembly of claim 1, wherein the outwardly curved connecting sections of the retention member connect the inwardly curved blocking tab sections and the arm sections such that a generally round shape is created.

10. The plate assembly of claim 1, wherein the retention member is continuous and uninterrupted from the end portion of a first arm section to the end portion of a second arm section.

11. A plate assembly, comprising:
a plate member having orifices and visualization orifices defined therethrough, each visualization orifice disposed adjacent a respective orifice, the plate member defining channels interconnecting respective orifices and visualization orifices, wherein each orifice is configured to receive a corresponding bone anchor member therethrough; and
a retention member, comprising:
  a plurality of inwardly curved blocking tab sections connected to each other by outwardly curved connecting sections, the retention member defining a longitudinal axis; and
  arm sections at each end of the retention member, each arm section extending linearly from a respective inwardly curved blocking tab section along the longitudinal axis and terminating at respective end portions disposed opposite the outwardly curved connection sections,
wherein the arm sections are parallel to and spaced apart from each other, the end portion of each arm section configured to be slidably received within a respective channel and visualization orifice of the plate member such that at least a portion of the end portion of each arm section is visible through the visualization orifice,
wherein the arm sections and the plurality of inwardly curved blocking tab sections define a gap therebetween, the gap being continuous and uninterrupted from the arm sections to the inwardly curved blocking tab sections.

* * * * *